United States Patent [19]

Hayashi et al.

[11] 4,409,105

[45] Oct. 11, 1983

[54] DRIED, STERILIZED, GAMMA-GLOBULIN-FIXED COLUMN AND A PROCESS FOR PREPARING THE SAME

[75] Inventors: Hiroshi Hayashi; Takao Kiyota, both of Fuji; Mitsuru Shibukawa, Yokohama, all of Japan

[73] Assignee: Asahi Kasei Kogyo Kabushiki Kaisha, Osaka, Japan

[21] Appl. No.: 323,338

[22] Filed: Nov. 20, 1981

[30] Foreign Application Priority Data

Dec. 18, 1980 [JP] Japan .............................. 55-178110

[51] Int. Cl.³ .............................................. B01J 8/02
[52] U.S. Cl. .................................... 210/679; 210/266; 210/287; 210/927; 260/112 B; 422/44; 502/402
[58] Field of Search ............... 210/679, 502, 927, 656, 210/287, 290, 266; 260/112 B; 128/214 R; 422/44

[56] References Cited

U.S. PATENT DOCUMENTS

| 3,857,931 | 12/1974 | Hager | 260/112 B |
| 3,946,105 | 3/1976 | Nagai et al. | 260/112 B |
| 4,202,775 | 5/1980 | Abe et al. | 210/927 |
| 4,246,351 | 1/1981 | Miyake et al. | 260/112 B |
| 4,261,828 | 4/1981 | Brunner et al. | 210/927 |
| 4,264,449 | 4/1981 | Dodd | 210/927 |

FOREIGN PATENT DOCUMENTS

| 2039490 | 8/1980 | United Kingdom | 260/112 B |
| 2075362 | 11/1981 | United Kingdom | 210/927 |

OTHER PUBLICATIONS

J. Biochem, 84, 559–567 (1798) vol. 84, No. 3, 1978.

Primary Examiner—Benoit Castel
Attorney, Agent, or Firm—Sprung, Horn, Kramer & Woods

[57] ABSTRACT

A dried, sterilized column containing a carrier-fixed γ-globulin capable of specifically combining with various harmful substances found in blood of patients suffering from certain diseases and acting as an antibody. The γ-globulin fixed column according to the present invention has a prolonged storage stability, and an excellent activity and safety even after the storage for a prolonged period of time as compared with unsterilized columns. Therefore, the γ-globulin fixed column according to the present invention may be advantageously used for medical instrument applications.

12 Claims, 1 Drawing Figure

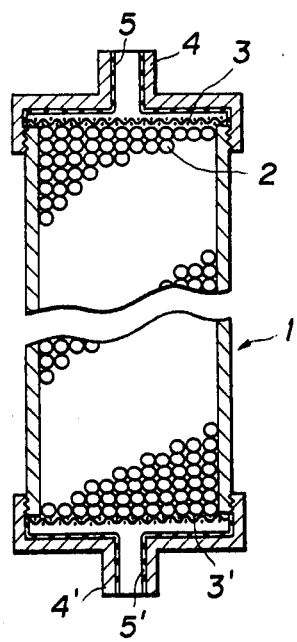
FIGURE

DRIED, STERILIZED, GAMMA-GLOBULIN-FIXED COLUMN AND A PROCESS FOR PREPARING THE SAME

This invention relates to a column containing a carrier-fixed γ-globulin capable of specifically combining with various harmful substances found in blood of patients suffering from certain diseases and acting as an antibody. More particularly, it is concerned with a γ-globulin-fixed column having a prolonged storage stability into which a carrier having the said γ-globulin held and fixed therein is packed in a dried and sterilized state.

Recently, it has been recognized that various harmful substances are found in large amounts in blood of patients suffering from certain diseases and specific removal of the harmful substances is useful for treatment of such diseases. There has been, therefore, made an attempt to develop an apparatus for removal of such harmful substances as seen, for example, in Japanese Patent Laid-Open Application No. 136379/1978.

However, the original purpose for development of such an apparatus has been directed to know how and what an uptake agent for such harmful substances should be held and used for removal of the harmful substance and thus it is the present status that sterilization of such apparatus for removal of the harmful substances has not been yet studied completely even still now as described in the description of the prior art in Japanese Patent Laid-Open Application No. 143588/1979.

For such a type of sterilization, there have been proposed, for instance, a method wherein bacteria-free enzymes obtained by filtration are aseptically carried on a sterilized carrier resin as seen in the above-mentioned Japanese Patent Laid-Open Application No. 143588/1979 or a method wherein sterilized filters for bacteria removal are attached to the upper end of both upper and lower ends of a fixed column assembled by a conventional procedure without consideration of sterilization as seen in Trans. Amer. Soc. Artif. Int. Organs, 18, 54–59 (1972).

However, the former sterilization method involves complicated assembling procedures of the apparatus, while the fixed column itself is not, in the latter method, sterilized. Therefore, it is difficult to say that there is sufficient safety to effect an extracorporeal perfusion of body fluids of patients suffering from diseases through the fixed column for treatment.

Moreover, none of the above-mentioned sterilized fixed columns are in a dried state and, therefore, they are insecure in prolonged storage. Generally, there have been no proposals on any dried, sterilized, antibody-fixed columns and, naturally, there have been no proposal like the present invention with regard to γ-globulin.

There is a growing demand for a safe sterilized column which can be used as an antibody fixed column for extracorporeal perfusion of body fluids from patients to specifically remove harmful substances. Nevertheless, the desired column has not been available because of difficulty in sterilization of the column after assembled, in view of speciality in the column wherein protein substances liable to undergo denaturation, for example, antibodies (especially γ-globulin), enzymes and the like are to be borne and fixed on a carrier.

The present inventors have earnestly made studies in order to provide a dried, sterilized column which is advantageous in storage and transportation. As a result, the present inventors have completed this invention which can make it feasible to assemble such a column on a commercial scale.

More specifically, this invention is directed to a γ-globulin-fixed column packed with a carrier bearing and fixing γ-globulin in a dried and sterilized state.

An object of this invention is to provide a medical instrument for removal of pathogenic substances solely from blood or body fluids of a patient by the use of the specificity of an antibody, particularly γ-globulin, through extracorporeal perfusion for the purpose of treatment.

The foregoing and other objects, features and advantages of the present invention will be apparent to those skilled in the art from the following detailed description taken in connection with the accompanying drawing in which:

The FIGURE shows one form of a γ-globlin fixed column according to the present invention.

The γ-globulin-fixed column according to the present invention will be illustrated in greater detail by referring to one example of the preparation thereof.

The term "γ-globulin" as used herein is meant to include, particularly, those classified as γ-globulin amongst antibodies capable of specifically combining with proteins by biochemical affinity, which appear beyond a normal level in blood of patients suffering from certain types of cancer and patients suffering from autoimmune diseases. As illustrative examples thereof, there may be mentioned anti-human-α-fetoprotein-γ-globulin or anti-human-ferritin-γ-globulin for removal of α-fetoprotein or ferritin which appears in blood and ascites of patients suffering from liver cancer or lung cancer; anti-HBs virus antigen γ-globulin for removal of HBs (B-type hepatitis virus) in blood of patients with hepatitis; anti-anti-nuclear antibody-γ-globulin to anti-nuclear antibody for removal of anti-nuclear antibody (immune complex) present in blood of patients with autoimmune diseases; specific γ-globulin for removal of antibody to acetylcholine-receptor in patients with myasthenia gravis; and mixtures thereof. Many other proteins participating in diseases than the foregoing have been found and would be discovered even later on. The present method is similarly applicable to any specific γ-globulin if prepared for removal of such proteins (pathogenic substances).

A method for the preparation of the antibody (in particular, γ-globulin), which may be employed in this invention, will be explained hereinbelow. The antibody can be obtained according to a conventional biochemical procedure (for example, see "Chemistry of Proteins I" in "Biochemistry Course I," edited by the Chemical Society of Japan, published from Tokyo Kagaku Dojin K.K.).

For instance, antigen protein (for example, α-fetoprotein or ferritin) can be recovered from blood or body fluids of a patient and purified to a higher purity by means of biochemical purification procedures. Then, the so purified protein can be used with various adjuvants (for example, complete Freund's adjuvant and the like) for immuno-sensitization to heterogenic animals (for example, goats, sheep, horses, rabbits and the like) to produce antiserum. The antiserum thus obtained is purified by such conventional biochemical procedures as precipitation fractionation with ammonium sulfate, ion exchanger chromatography, affinity-chromatography and the like to yield γ-globulin fraction. It is to be noted that, upon the protein (pathogenic substance) to be removed, there is employed γ-globulin specific thereto.

The carrier resin for bearing and fixing γ-globulin in this invention will be discussed hereinbelow. There may be employed any of those resins commonly employed for bearing and fixing such proteins as antibody or enzyme. Illustratively, there may be mentioned, for example, agarose-type resins, polyvinyl alcohol-type resins, polyacrylamide-type resins, crosslinked dextran resins, cellulose, porous silica beads and the like.

In order to remove specifically proteins such as pathogenic substances from blood of patients, in particular, there are demands that there is not seen non-specific adsorption of proteins, substances and the like unrelating to removal, that a column volume should be minimized and a volume of blood or body fluids to be taken outside the body should be reduced as far as possible so as to lighten the burden on patients and also a bearing and fixing volume of γ-globulin as a ligand per unit volume should be of a high level and that there is no decomposition during storage and use with an excellent chemical stability when borne and, further, there is an excellent mechanical hydrodynamic characteristic property to keep a sufficient perfusion speed. Upon such demands, there are preferably used agarose resins, polyvinyl alcohol-type resins and agarose-type resins such as crosslinked agarose resins, especially as fixing resins and they are preferably used in a granular shape.

For combining the above-mentioned γ-globulin with the bearing or carrier resins, there may be used the so-called well-known methods, such as physical adsorption, ionic bonding, inclusion, covalent bonding and the like. A particularly preferable combination method is the covalent bonding one in view of stability in sterilization and prolonged stability. More specifically, chemical covalent bonding can be effected with the reactive group of γ-globulin, such as a hydroxyl group, an amino group, a carboxyl group, a thiol group and the like by the use of a bifunctional crosslinking agent, e.g. glutaraldehyde or a coupling agent, e.g. carbodiimide, cyanogen bromide, Woodward's reagent, diazotating agent and the like, in utilization of reactivity in functional groups present in the carrier resin, e.g. a carboxyl group, an amino group, a hydroxyl group, a halogen atom and the like. An amount of γ-globulin to be carried on the bearing resin is not critical, but an amount of 5 mg to 100 mg of γ-globulin per cc of the resin is preferable.

The freeze-drying or lyophilization of a carrier having γ-globulin borne thereby and fixed thereto will be illustrated hereunder.

Where a freeze-dryable resin is used as a carrier (for example, polyvinyl alcohol type resins, polyacrylamide type resins and the like), it is sufficient to freeze-dry the carrier in a state in which γ-globulin is borne thereby and fixed thereto in an aqueous solution as such or after hydro-extracting and then vacuum-drying it under reduced pressure.

However, where an agarose type resin preferably usable for the carrier is employed as a bearing, fixing carrier, structure within and outside the resin may undergo breakage because of freezing of water on freeze-drying, if freeze-dried in an aqueous solution as it stands, and, when re-swollen, a volume is reduced because of non-restoration in porosity and also efficiency is remarkably lowered.

It has been heretofore reported (See a brochure issued from Pharmacia Finechemical Co., Ltd.) that the above-recited phenomena can be prevented by using dextran-lactose in freeze-drying the fixed column with agarose-type resins. However, since the present invention is directed to medical instruments, the above-mentioned lowered efficiency is at issue, but, even if a resin which can be freeze-dried in an aqueous solution is employed, not only safety but also period of time for re-swelling, sterilization efficiency and prolonged storage stability are extremely important.

As a result of studies in consideration of the foregoing, it has been found that re-swelling time can be reduced and also a prolonged storage stability can be attained and, further surprisingly, lowering of efficiency can be prevented even in the case of agarose-type resins used as the carrier resin, by the use of the under-defined sugar alone or under certain concentration conditions, as compared with the case wherein direct freeze-drying is done from an aqueous solution or wherein freeze-drying is done in the presence of dextran-lactose.

Namely, the preferred freeze-drying method consists in conducting lyophilization in a 1–20% aqueous solution, preferably a 2–15% aqueous solution, of a sugar selected from the group consisting of lactose, mannose, sucrose and glucose, and it is particularly preferred to effect freeze-drying in a 5–15% aqueous solution of glucose.

It has been known that an aqueous solution of any of various sugars is applied in freeze-drying for storage of various proteins and bacteria (for example, see "Freezing.drying and Protective Materials," issued from The Tokyo University Shuppan Kai, 1972), but there has been found nothing except for this invention where a sugar alone is used in freeze-drying the fixed column having γ-globulin carried and fixed thereon for such purposes like this invention.

The column according to this invention can be prepared by any of the methods wherein a required amount of the resin having γ-globulin fixed thereto is beforehand freeze-dried according to the aforesaid method, packed into a given column vessel and then sterilized or wherein the said resin in the form of a solution is packed into a desired vessel, washed and substituted thoroughly with an aqueous solution of the sugar for freezing, freeze-dried as it is in the said vessel and then sterilized. The sterilization may be effected with the column enclosed in a suitable vessel or package capable of keeping a sterilized state such as a commercially available bag for ethylene oxide sterilization and the like.

The sterilization method which is contemplated in this invention will be more fully illustrated below.

If the fixed column resin bearing γ-globulin is subjected to sterilization under such a condition that the resin is suspended in an aqueous solution, there is such an advantage that it is employable as such when used. However, the sterilization means in that case are limited to only those by heat or γ-ray irradiation. Though the present inventors have indeed studied such sterilization means, it has been found that denaturation of γ-globulin and a protein, and decomposition of the carrier resin are brought about and hence the said means are not practically feasible although sterilized. The present inventors have made earnest studies with the intention that sterilization may be accomplished by other means than heating or γ-ray irradiation by keeping the column in a dried state as discussed above and then succeeded in settlement of this problem.

More specifically, the γ-globulin fixed column thus produced in the above-mentioned manner can be subjected to lyophilization according to the aforesaid method to yield a γ-globulin fixed resin in a dried state. Thereafter, sterilization can be conducted with ethylene oxide or propylene oxide gas to obtain a dried, sterilized γ-globulin-fixed column with a superior storage stability.

Though thermal or γ-ray sterilization has been attempted under the similar dried condition, denaturation of γ-globulin could be incurred similarly to the case of suspension in water and sterilization itself could be accomplished with no practical usefulness.

The sterilized column according to this invention is in not only sterilized state but dried state and has superior characteristics not disclosed in the prior art as medical instruments in that leakage of liquid during transportation, mechanical break on the resin and the like do not occur and that it is very stable even over a prolonged period of storage.

The present column thus produced can remove pathogenic substances which appear beyond a normal level in blood or body fluids of patients suffering from certain diseases by specific combination thereof with antibody to the said substances (in particular, γ-globulin) and thus become very useful medical instruments to be employed in a set with extracorporeal perfusion.

As explained hereinabove, the sterilized γ-globulin fixed column according to this invention cannot bring about any leakage of liquid or break as compared with the prior art column with regard to storage or transportation because of its dried state, and shows excellent characteristics of high stability over a prolonged period of storage and simple storage conditions because of its sterilized state and, additionally, can ensure safety, which is of utmost importance for medical purposes. And further, the present method has an advantage in that any particularly complicated assembling procedures are not required since sterilization is effected after the column is assembled. Thus, it can be said that the present method is highly excellent as not seen in the prior art.

The present invention will be more concretely illustrated by way of the following examples, which should not be construed to be limiting the scope of the present invention.

EXAMPLE 1

Ascites from a patient suffering from liver cancer was roughly purified by conventional biochemical procedures, i.e. fractionation with ammonium sulfate and chromatography with an ion exchange resin to obtain α-fraction, which was then subjected twice to absorption procedures with normal human antiserum, thereby α-fetoprotein being purified. The α-fetoprotein was 90% purity. Since the α-fetoprotein was contaminated with albumin and transferrin, re-absorption was effected with a Con A column and anti-transferrin serum to obtain α-fetoprotein of a purity of 99% (disc electrophoresis, 70% acrylamide gel, pH 8.3). The so obtained α-fetoprotein was administered to 4–5 times to sheep at the back thereof at 7–15 days intervals in an amount of 1 mg per ounce to produce anti-human-α-feto-protein antiserum (sheep).

The antiserum thus produced was subjected to fractionation with ammonium sulfate and DEAE-ion exchange resin chromatography to obtain γG fraction as an antibody. The said γG fraction has been found to have satisfactory specificity and titre by Ouchterlony's test (immuno double diffusion test).

Then, 4 g of the said γG fraction ($E_{280}^{1\%}=14.3$) was combined with 200 cc of a commercially availabe crosslinked agarose resin, Sepharose GL-4B (manufactured and sold by Pharmacia Finechemical Co., Ltd). Namely, 200 cc of Sepharose CL-4B was washed well with distilled water, suspended in 200 ml of water and 12 g of cyanogen bromide was added. The suspension was stirred. Reaction was conducted over 8 minutes while maintaining pH at 10-11 with a 2 N aqueous solution of sodium hydroxide to activate Sepharose CL-4B. Then, the mixture was rapidly washed with 2 liters of a cold 0.1 M aqueous solution of sodium hydrogencarbonate, suction-filtered, and then suspended in 200 ml of a 0.1 M sodium hydrogencarbonate buffer (pH 8.3) containing 0.5 M sodium chloride. To the suspension was added 4 g of the γG fraction and reaction was effected at 4° C. over 14 hours under gentle stirring. After completion of the reaction, the resulting mixture was washed with 1 liter of a 0.1 M sodium hydrogencarbonate buffer containing 0.1 N NaCl and subsequently re-suspended in a 1 M aqueous solution of ethanolamine (pH 9) and reaction was carried out at room temperature for 2 hours with gentle stirring. Then, the resin was washed again with 1 liter of a 0.1 M sodium hydrogencarbonate buffer containing 0.1 M NaCl and then with 1 liter of a 0.1 M acetate buffer (pH 4.0) and again with 1 liter of the said sodium hydrogencarbonate buffer. After washing with 500 ml of a 5 M aqueous solution of urea, the resin was finally washed with 2 liters of physiological sodium chloride solution. The resin thus combined with antibody was stored in the suspended state in physiological sodium chloride solution.

As one embodiment, the invention will become more apparent in the light of the accompanying drawing. Referring to FIGURE wherein the fixed resin obtained above was packed into a 50 cc volume vessel made of acrylic resin having 500-mesh nylon filters arranged at both ends thereof to produce an antibody-fixed resin column. Now referring to the drawing, the structure of the said column will be more fully explained. The resin 2 having antibody borne thereby and fixed thereto is packed into the cylindrical vessel 1. The packed resin in the vessel 1 is covered, at its top and bottom, with filters 3 and 3', respectively. As depicted in FIGURE, caps 4 and 4' have openings which serve as an inlet and an outlet for liquid. The caps 4 and 4' also have, on their respective inner surfaces, protective layers 5 and 5' formed of a silicone lining material, and are fitted over the vessel 1 at its top and bottom, respectively, as depicted in the FIGURE.

Then, the column was exchanged by passing 500 cc of a 8% aqueous solution of glucose therethrough, freezed and then dried in vacuo.

The column was sealed in a sterile bag, treated with gaseous ethylene oxide at 40° C. for 5 hours and replaced with air for 1 hour to form a sterilized, dried antibody-fixed column A.

EXAMPLE 2

Human ferritin was purified according to the Niitsu et al method (See "Igakunoayumi" vol. 95, No. 1, p. 12).

Antiserum was obtained by immunizing several times domestic rabbits using 0.1 mg of ferritin together with complete Freund's adjuvant and collecting whole blood after one and half months.

Then, 1 g of the γG fraction as purified in the same manner as in the Example 1 was combined with 100 ml of agarose resin, Sepharose 6B (manufactured and sold by Pharmacia Finechemical Co., Ltd.) by the use of cyanogen bromide according to a conventional method to give a fixed resin.

The said fixed resin was packed into a vessel, exchanged with a 10% aqueous solution of mannose and then freeze-dried.

Then, the said column was sealed in a sterile bag, and sterilized with gaseous ethylene oxide at 40° C. to give the anti-ferritin antibody fixed column B.

COMPARATIVE EXAMPLE 1

Following the same procedures as in Example 1, a resin having anti-human-α-fetoprotein antibody fixed thereto was prepared. The said resin was rinsed well with physiological sodium chloride solution, packed into a 50 cc volume column made of a heat-resistant resin(polycarbonate) and then steam-sterilized in an autoclave at 120° C. for 20 minutes. The resulting column was used for the under-mentioned test as Column C.

COMPARATIVE EXAMPLE 2

Following the same procedures as in Example 2, a resin having anti-human-ferritin antibody fixed thereto was prepared. The said resin was rinsed well with physiological sodium chloride solution, packed into a 50 cc column made of polystyrene and then sterilized by irradiation of γ-ray with 2.5 M rad. The resulting column was used for the under-mentioned test as Column D.

COMPARATIVE EXAMPLE 3

Following the same procedures as in Example 1, a resin having anti-human-α-fetoprotein antibody fixed thereto was prepared. The said resin was packed into a 50 cc column and washed well with physiological sodium chloride solution. The Column E was used for the under-mentioned test without freeze-drying and sterilization.

COMPARATIVE EXAMPLE 4

Following the same procedures as in Example 1, a resin having anti-human-α-fetoprotein antibody fixed thereto was prepared. The said resin was packed into a 50 cc column, washed well with sterilized physiological sodium chloride solution and bacteria-removed, sterilized distilled water and then freeze-dried as such. The column was used for the under-mentioned test as Column F.

COMPARATIVE EXAMPLE 5

Following the same procedures as in Example 2, a resin having anti-human-ferritin antibody fixed thereto was prepared. The said resin was packed into a 50 cc column and washed well with physiological sodium chloride solution. The Column G was used for the under-mentioned test without freeze-drying and sterilization.

EXAMPLE 3

Following the same procedures as in Example 1, a resin having anti-human-α-fetoprotein antibody fixed thereto was prepared. The said resin was packed into a 50 cc column, washed with physiological sodium chloride solution, washed and exchanged sufficiently with a 10% aqueous solution of lactose and then freeze-dried. Then, it was sealed in a sterile bag and sterilized with 35% ethylene oxide gas. The column was used for the under-mentioned test as Column H.

EXAMPLE 4

Following the same procedures as in Example 2, a resin having anti-human-ferritin antibody fixed thereto was prepared. The said resin was packed into a 50 cc column, washed with physiological sodium chloride solution, and exchanged sufficiently with a 5% aqueous solution of sucrose and then freeze-dried. Then, it was sealed in a sterile bag and sterilized with gaseous ethylene oxide. The column was used for the under-mentioned test as Column I.

COMPARATIVE EXAMPLE 6

The procedures were followed according to the teachings in "Experiments and Applications, Affinity-Chromatography," by Chihata et al., issued from Kodansha.

Dry acrylamide gel (Biogel-p-60, manufactured and sold by Bio Rab Co., Ltd.) was swollen in water overnight and then a 6 M aqueous solution of hydrazine hydrate previously heated at 50° C. for 60 minutes was added to an equal volume of the swollen gel suspension. Reaction was conducted at 50° C. overnight. The resulting gel derivative was thoroughly washed with a 0.1 M sodium chloride solution.

The so produced acrylamide gel-hydrazide derivative (200 mg) was washed well with 100 ml of 0.3 N hydrochloric acid containing 0.1 M sodium chloride and then with 100 ml of 0.3 N hydrochloric acid. Thereafter, the derivative was suspended in 30 ml of 0.3 N hydrochloric acid and 2 ml of a 1 M sodium nitrite solution was added thereto at 4° C. After reaction in ice-water for 20 minutes, the resultant acylazide derivative was collected by filtration and immediately washed successively with a 0.3 N aqueous hydrochloric acid solution, 0.1 M sulfamic acid and a cold water.

The acylazide derivative thus obtained was dissolved in a 0.1 M sodium borate solution and added to 12 ml of a 1% anti-human-α-fetoprotein antibody solution at 4° C. Reaction was effected with stirring for 2 hours. After addition of a 1 M aqueous ammonia solution and 4 ml of 1 M ammonium chloride, further reaction was continued for 2 hours.

Then, the fixed antibody resin was packed into two columns, respectively, and one of them was washed well with 0.2 M sodium chloride and used for the under-mentioned test as Column J.

EXAMPLE 5

Another column in the above Comparative Example 6 was washed well with physiological sodium chloride solution, exchanged with a 10% aqueous solution of glucose and then freeze-dried. After sterilization with 35% ethylene oxide gas, the column was used for the under-mentioned test as Column K.

COMPARATIVE EXAMPLE 7

50 g of agarose resin, Sepharose 6B (manufactured and sold by Pharmacia Finechemical Co., Ltd.) was washed well with distilled water, 50 ml of 1,4-butanediol diglycidyl ether of 50 ml of 0.6 M NaOH containing 100 mg of sodium boron hydride were added thereto and then reaction was effected at room temperature while shaking for 8 hours. Then, the resin was placed onto a glass filter and washed well with water to produce the activated resin.

In 50 ml of a 1 M aqueous sodium carbonate (pH 11.5) solution was dissolved 1 g of anti-human-ferritin antibody and 50 ml of the above activated resin was added to the resulting solution and then reaction was conducted at 25° C. while shaking for 16 hours. Thereafter, the resin was placed into a 1 M aqueous solution of ethanolamine and reaction was carried out at room temperature overnight while allowed to stand. After washing well with physiological sodium chloride solution, the resin was packed into a 50 cc column, which was used for test as Column L.

EXAMPLE 6

The column as prepared in the same manner as in Comparative Example 6 was exchanged enough with a 8% aqueous solution of glucose, freeze-dried and then sterilized with 35% ethylene oxide gas to form Column M.

EXAMPLE 7

Following the same procedures as in Example 1, 4 g of the anti-human-α-fetoprotein γG fraction obtained in the same manner as in Example 1 was combined with 200 cc of the crosslinked polyvinyl alcohol resin produced as described below and previously activated by cyanogen bromide.

The thus produced resin having antibody fixed thereto was washed well with physiological sodium chloride solution previously sterilized and with sterilized distilled water and hydro-extracted by suction filtration. The resin was placed in a sterile bag, cooled to −20° C. by means of a freeze-drying machine (manufactured and sold by LABCONCO, CO., LTD.) and then dried in vacuo.

The resulting dried resin was packed into the same vessel as in Example 1, placed again in a gas-sterilized bag, treated with 35% ethylene oxide at 40° C. for 4 hours and thoroughly exchanged with air to remove the residual ethylene oxide, whereby producing the sterilized, dried, antibody-fixed Column N.

Similarly, sterilization with propylene oxide in place of the 35% ethylene oxide gave the antibody-fixed Column O.

These columns were used for tests.

REFERENTIAL EXAMPLE

Preparation of a Crosslinked Polyvinyl Alcohol Resin

A homogeneous mixture of 100 g of vinyl acetate, 24.1 g of triallyl isocyanurate (X=2.00), 124 g of ethyl acetate, 124 g of heptane, 3.1 g of polyvinyl acetate (polymerization degree: 500) was placed into a flask with 400 ml of water containing polyvinyl alcohol 1% by weight, sodium dihydrogen phosphate dihydrate 0.05% by weight and disodium hydrogen phosphate dodecahydrate 1.5% by weight. After thorough stirring suspension polymerization was carried out by heating with stirring at 65° C. for 18 hours and then at 75° C. for further 5 hours to give granular copolymer. After filtration, washing with water and extraction with acetone, transesterification of the copolymer was effected in a solution of 46.5 g of sodium hydroxide in 2 liters of menthanol at 40° C. for 18 hours. The resulting grain had an average grain size of 150 μm, a hydroxyl density (q OH) of 13 meq/g, a water regain of 4.4 gr/g and a specific surface area of 10 m$^2$/g in a dry sate. The resin thus obtained had very excellent resin properties.

By using varied compositions of starting materials, there were prepared similar resins having various properties. There were observed a difference in the degree of activation with cyanogen bromide and a change in antibody combining ability, which resulted in somewhat difference in removal efficiency. However, there can be generally obtained the resins which fulfil the objects of this invention.

It should be noted that the polyvinyl alcohol resins employable in this invention are not to be limited to the above Referential Example.

Experiment

With respect to Column's A to O as prepared in the above Examples and Comparative Examples, there were conducted efficiency test, re-swelling time test, aseptic test and storage test. The test procedures and results therefrom are shown below.

Test Procedures

(1) Test For Efficiency

A given amount of physiological sodium chloride solution containing standard α-fetoprotein or ferritin was passed through the column. The column was washed well with physiological sodium chloride solution and then the adsorbed α-fetoprotein or ferritin was eluted with 0.1 M glycine-hydrochloric acid buffer (pH2.8). Eluates were in turn neutralized with 1 M glycine-sodium hydroxide buffer (pH 11.5) and amounts of α-fetoprotein or ferritin thus adsorbed were measured. According to Lowry method and EIA method [following the Hibi et al method, Gann, 69, 67–75 (1978)], a charged solution, a passing-through solution and an eluted solution were measured, respectively. Efficiency was calculated according to the following equation:

$$\text{Efficiency} = \frac{\text{Adsorbed amount on each column}}{\text{Adsorbed amount on column E or G}} \times 100$$

(2) Tests for re-swelling time and volume

Equal amounts of the resins having antibody fixed thereto one of which has been subjected to freeze-drying and sterilization treatment and the other not subjected to the treatment were individually weighed into a graduated glass tube and physiological sodium chloride solution was added thereto. Time required for re-swelling and final volume were measured. Degree of re-swelling was calculated according to the following equation:

$$\text{Degree of re-swelling} = \frac{\text{Volume after re-swollen (suspended)}}{\text{Volume before freeze-dried and sterilized (suspended)}} \times 100$$

(3) Sterility Test

The test was in conformity to the sterility test in the pharmacopoeia of Japan. The results are expressed in terms of the bacterial numbers, namely, 0(−), 1-100(+), 100<(++).

(4) Storage Test

The following two tests were made in the sterility test and efficiency test.

| | |
|---|---|
| (i) Temperature of 4° C. | 1 month, 3 months, 6 months, 12 months |
| (ii) Temperature of 25° C. | 1 month, 3 months, 6 months, 12 months |

Efficiency was calculated in the same fashion as in the above test (1) upon the ratio to adsorbed amount of Column E or G.

The test results are summarized in the following Table.

column after storage at 25° C. over 6 months kept 95% efficiency and aseptic state.

EXAMPLE 9

It was known that an anti-acetylcholine receptor antibody is found in blood of patients suffering fom myasthenia gravis and closely related to its etiology. The said receptor antibody was specifically isolated from blood of the patients by using an acetylcholine receptor. Thereafter, enzymatic decomposition and purification were effected according to the above-recited "Chemistry of Protein I, Biochemical Experiment Course 1" edited by the Japanese Biochemical Society, issued from Tokyo Kagaku Dojin for obtaining the antibody to Fab of the said receptor antibody,

TABLE 1

| | Column | Affinity volume (n = 5 average) | ratio to E Efficiency ratio to G | Re-swelling time (n = 5 average) | Volume ratio after re-swollen | Sterility test | | Lowered Efficiency | | | | | Sterility test | | | |
|---|---|---|---|---|---|---|---|---|---|---|---|---|---|---|---|---|
| | | | | | | | | 1 mo. | 3 mos. | 6 mos. | 12 mos. | | 1 mo. | 3 mos. | 6 mos. | 12 mos. |
| Ex. 1 | A | 490 μg/cc | 98 to E | 2' 37" | 99 | (−) | 4° C. | 98 | 98 | 98 | 98 | | (−) | (−) | (−) | (−) |
| | | | | | | | 25 | 98 | 98 | 97 | 97 | | | | | |
| Ex. 2 | B | 147 μg/cc | 98 to G | 2' 40" | 90 | (−) | 4 | 98 | 98 | 98 | 98 | | (−) | (−) | (−) | (−) |
| | | | | | | | 25 | 98 | 97 | 97 | 97 | | | | | |
| Comp. Ex. 1 | C | 0 μg/cc | 0 | — | — | (−) | 4 | — | — | — | — | | — | — | — | — |
| | | | | | | | 25 | | | | | | | | | |
| Comp. Ex. 2 | D | 35 μg/cc | 23 to G | — | — | (−) | 4 | — | — | — | — | | — | — | — | — |
| | | | | | | | 25 | | | | | | | | | |
| Comp. Ex. 3 | E | 500 μg/cc | 100 | — | — | (++) | 4 | 98 | 95 | 90 | 80 | 4° C. | + | + | + | ++ |
| | | | | | | | 25 | 70 | 65 | 65 | 60 | 25 | ++ | ++ | ++ | ++ |
| Comp. Ex. 4 | F | 325 μg/cc | 65 to E | 5' 17" | 30 | (+) | 4 | 65 | 64 | 60 | 60 | 4 | + | + | ++ | ++ |
| | | | | | | | 25 | 50 | 32 | 30 | 30 | 25 | ++ | ++ | ++ | ++ |
| Comp. Ex. 5 | G | 150 μg/cc | 100 | — | — | (++) | 4 | 88 | 80 | 75 | 75 | 4 | + | ++ | ++ | ++ |
| | | | | | | | 25 | 70 | 65 | 60 | 55 | 25 | ++ | ++ | ++ | ++ |
| Ex. 3 | H | 395 μg/cc | 79 to E | 5' 03" | 74 | (−) | 4 | 79 | 79 | 79 | 77 | | (−) | (−) | (−) | (−) |
| | | | | | | | 25 | 79 | 78 | 78 | 78 | | | | | |
| Ex. 4 | I | 130 μg/cc | 87 to G | 4' 15" | 85 | (−) | 4 | 87 | 87 | 87 | 87 | | (−) | (−) | (−) | (−) |
| | | | | | | | 25 | 87 | 85 | 85 | 85 | | | | | |
| Comp. Ex. 6 | J | 200 μg/cc | 100 | — | — | (+) | 4 | 90 | 88 | 86 | 80 | 4 | + | + | ++ | ++ |
| | | | | | | | 25 | 88 | 80 | 65 | 45 | 25 | ++ | ++ | ++ | ++ |
| Ex. 5 | K | 196 μg/cc | 98 to J | 5' 45" | 98 | (−) | 4 | 98 | 97 | 97 | 95 | | (−) | (−) | (−) | (−) |
| | | | | | | | 25 | 98 | 98 | 98 | 97 | | | | | |
| Comp. Ex. 7 | L | 100 μg/cc | 100 | — | — | (+) | 4 | 98 | 97 | 90 | 90 | 4 | + | + | ++ | ++ |
| | | | | | | | 25 | 85 | 80 | 70 | 60 | 25 | ++ | ++ | ++ | ++ |
| Ex. 6 | M | 97 μg/cc | 97 to L | 3' 12" | 98 | (−) | 4 | 97 | 97 | 97 | 96 | | (−) | (−) | (−) | (−) |
| | | | | | | | 25 | 97 | 96 | 96 | 96 | | | | | |
| Ex. 7 | N | 490 μg/cc | 98 to E | 2' 10" | 99 | (−) | 4 | 98 | 98 | 98 | 98 | | (−) | (−) | (−) | (−) |
| | | | | | | | 25 | 98 | 98 | 97 | 97 | | | | | |
| | O | 480 μg/cc | 96 to E | 2' 15" | 99 | (−) | 4 | 96 | 96 | 96 | 96 | | (−) | (−) | (−) | (−) |
| | | | | | | | 25 | 96 | 96 | 96 | 95 | | | | | |

EXAMPLE 8

From serum of patients suffering from hepatitis was isolated B-type hepatitis virus (HBs). The antibody to HBs antigen was prepared in the same manner as in Example 1 and then purified to give γ-globulin fraction.

As the carrier for fixation of the said γ-globulin, there was used a commercially available cyanogen bromide-activated Sepharose 4B (manufactured an sold by Pharmacia Finechemical Co., Ltd.) wherein 10 mg of γ-globulin per 1 cc of the resin was borne or carried. After efficiency test was done with HBs antigen positive serum, the resin was packed into a 1 cc column vessel, washed and exchanged well with a 10% aqueous solution of glucose, freeze-dried and then sterilized with gaseous ethylene oxide.

The column thus prepared showed only 2% of lowered efficiency upon lyophilization and sterilization, as compared with the unsterilized case, similarly to the column fixed α-fetoprotein antibody and ferritin antibody and ensured its aseptic condition and safety though sterilized after once applied. Moreover, the thereby giving Fab fraction of purified acetylcholine receptor antibody. Subsequently, antiserum was taken from the Fab fraction in the same manner as in Example 1 and γ-globulin fraction was obtained from the said antiserum. The so obtained γ-globulin fraction was absorbed into human serum to produce non-absorptive γ-globulin fraction. The latter γ-globulin fraction was borne and fixed on activated Sepharose 6B according to the same manner as in Comparative Example 7 to prepare a column for treating serious myasthenia.

With respect to column prepared above, there was conducted a test for efficiency by the use of blood plasma from serious myasthenia and the column was then washed well and exchanged with a 7% aqueous solution of mannose, lyophilized and then sterilized with gaseous ethylene oxide.

This sterilized column showed only 5% of lowered efficiency similarly to the column of Example 8, as compared with the unsterilized case, and also passed sterility test. Additionally, 94% efficiency was kept after storage at 25° C. over 3 months, with alteration being hardly seen and aseptic state being maintained.

As apparent from the above-recited Examples and Comparative Examples, the dried, sterilized antibody fixed resin column prepared according to this invention can hold a satisfactory activity and stability even over a prolonged storage period because of its sterilized and dried state, as compared with an unsterilized column. Besides, the column is secured for safety which is regarded as extremely significant as medical instruments. This invention may provide a way to practically utilize this type of vital protein fixed column as medical instruments hereafter.

What is claimed is:

1. A γ-globulin fixed column comprising a vessel, a pair of spaced filter screens, an inlet, an outlet and carrier resin having γ-globulin borne thereby and fixed thereto and packed in a dried and sterilized state into the vessel between the screens, the sterilization having been effected with ethylene oxide gas or propylene oxide gas.

2. A column according to claim 1, wherein said borne γ-globulin is at least one member selected from the group consisting of anti-human-α-fetoprotein-γ-globulin, anti-human-ferritin-γ-globulin, anti-B type hepatitis virus antigen γ-globulin, anti-anti-nuclear antibody-γ-globulin and anti-human-acetylcholine receptor antibody-γ-globulin.

3. A column according to claim 1, wherein said carrier is of an agarose type resin.

4. A column according to claim 1, wherein said carrier is of a polyvinyl alcohol type resin.

5. A process for preparing a dried, sterilized γ-globulin-fixed column which comprises subjecting carrier resin having γ-globulin borne thereby and fixed thereto to drying treatment and then to sterilization with ethylene oxide gas or propylene oxide gas.

6. A process according to claim 5, wherein said drying treatment is lyophilization.

7. A process according to claim 6, wherein prior to the lyophilization said γ-globulin fixed column is equilibrated with a 1–20% aqueous solution of a sugar selected from the group consisting of mannose, lactose, sucrose and glucose.

8. A process according to claim 7, wherein said aqueous solution of a sugar is a 5–15% aqueous solution of glucose.

9. A process according to any of claims 5 to 8, wherein said borne γ-globulin is at least one member selected from the group consisting of anti-human-α-fetoprotein-γ-globulin, anti-human-ferritin-γ-globulin, anti-B type hepatitis virus antigen γ-globulin, anti-anti-nuclear antibody-γ-globulin and anti-human-acetylcholine receptor antibody-γ-globulin.

10. A process according to claim 5, wherein said carrier is of an agarose type resin.

11. A process according to claim 5, wherein said carrier is of a polyvinyl alcohol type resin.

12. A process according to claim 5, wherein said sterilization is effected using ethylene oxide gas.

* * * * *